US012629244B2

(12) United States Patent
Heo et al.

(10) Patent No.: US 12,629,244 B2
(45) Date of Patent: May 19, 2026

(54) TISSUE EXPANDER FOR BREAST RECONSTRUCTION CAPABLE OF MMP SENSOR-BASED REAL-TIME CAPSULAR CONTRACTURE MONITORING AND TREATMENT, AND PATIENT INFORMATION SYSTEM LINKED THERETO

(71) Applicants: Seoul National University Hospital, Seoul (KR); Research & Business Foundation Sungkyunkwan University, Suwon-Si (KR)

(72) Inventors: Chan Yeong Heo, Yongin-Si (KR); Sun-Young Nam, Anyang-Si (KR); Jae Heon Jeong, Seongnam-Si (KR); Dayoung Youn, Seongnam-Si (KR); Tai Myoung Chung, Seoul (KR)

(73) Assignees: Seoul National University Hospital, Seoul (KR); Research & Business Foundation Sungkyunkwan University, Suwon-Si (KR)

( * ) Notice: Subject to any disclaimer, the term of this patent is extended or adjusted under 35 U.S.C. 154(b) by 1037 days.

(21) Appl. No.: 17/777,237

(22) PCT Filed: Nov. 18, 2020

(86) PCT No.: PCT/KR2020/016237
§ 371 (c)(1),
(2) Date: Nov. 10, 2022

(87) PCT Pub. No.: WO2021/101232
PCT Pub. Date: May 27, 2021

(65) Prior Publication Data
US 2023/0128540 A1     Apr. 27, 2023

(30) Foreign Application Priority Data
Nov. 18, 2019     (KR) ........................ 10-2019-0147946

(51) Int. Cl.
*A61F 2/12*          (2006.01)

(52) U.S. Cl.
CPC ........ *A61F 2/12* (2013.01); *A61F 2250/0002* (2013.01); *A61F 2250/0003* (2013.01);
(Continued)

(58) Field of Classification Search
CPC ............... A61F 2/12; A61F 2250/0002; A61F 2250/0003; A61F 2250/0068;
(Continued)

(56) References Cited

U.S. PATENT DOCUMENTS

2011/0152913 A1     6/2011   Jones et al.
2013/0150685 A1*    6/2013   Toth ..................... A61B 5/4848
                                                          600/302
(Continued)

FOREIGN PATENT DOCUMENTS

EP           3132772 A2      2/2017
JP        2008-513182 A      5/2008
(Continued)

OTHER PUBLICATIONS

"International Search Report"; prepared for application No. PCT/KR2020/016237; Feb. 25, 2021; 8 pages.
(Continued)

*Primary Examiner* — Suzette J Gherbi
(74) *Attorney, Agent, or Firm* — Jackson Walker LLP

(57) ABSTRACT

Disclosed are a tissue expander for breast reconstruction comprising an MMP sensor and thus being capable of real-time capsular contracture monitoring and treatment, and a patient information system linked thereto. According to these, a patient or medical staff can easily check and evaluate capsular contracture, which may occur when wearing a tissue expander for breast reconstruction, and whether inflammation, a side effect, or the like is caused thereby, even outside the human body in real time. Accordingly, before or when capsular contracture occurs, effective treatment and response are possible.

13 Claims, 7 Drawing Sheets

(52) U.S. Cl.
CPC . *A61F 2250/0068* (2013.01); *A61F 2250/008* (2013.01); *A61F 2250/0096* (2013.01)

(58) Field of Classification Search
CPC ....... A61F 2250/008; A61F 2250/0096; A61B 90/02; A61B 5/412; A61B 5/4851; A61B 5/07; A61B 5/0002; A61B 5/24; A61B 5/6847; C12Q 1/005; C12Q 1/37; G01N 2333/96494
See application file for complete search history.

(56) References Cited

U.S. PATENT DOCUMENTS

| | | | | |
|---|---|---|---|---|
| 2013/0338770 | A1* | 12/2013 | Boyden | A61B 5/076 623/8 |
| 2018/0193327 | A1 | 7/2018 | Bresnick | |
| 2021/0045640 | A1* | 2/2021 | Poltorak | A61B 5/369 |
| 2023/0067762 | A1* | 3/2023 | Irrgang | H04N 13/246 |

FOREIGN PATENT DOCUMENTS

| | | |
|---|---|---|
| JP | 2009-544013 A | 12/2009 |
| JP | 2016-526926 A | 9/2016 |
| KR | 10-2010-0105254 A | 9/2010 |

OTHER PUBLICATIONS

Lee, Jae Woong, "Electrical Tunneling Biosensor for Detecting MMP-9 Using Concentric Electrode Device", The master's thesis: Department of Electrical and Computer Engineering, Seoul National University Graduate School, 2016.

Ulrich, Dietmar et al., "Effect of tissue inhibitors of metalloproteinases and matrix metalloproteinases on capsular formation around smooth and textured silicone gel implants", Aesthetic Plastic Surgery, 2009, vol. 33, pp. 555-562.

* cited by examiner

TISSUE EXPANDER FOR BREAST RECONSTRUCTION CAPABLE OF MMP SENSOR-BASED REAL-TIME CAPSULAR CONTRACTURE MONITORING AND TREATMENT, AND PATIENT INFORMATION SYSTEM LINKED THERETO

TECHNICAL FIELD

The present specification relates to a tissue expander for breast reconstruction capable of a human body insertion-type MMP sensor-based real-time capsular contracture monitoring and treatment, and a patient information system linked thereto.

[National R&D Project Supporting the Present Invention]
[Project ID number]1465029459
[Name of Ministry] Ministry of Health and Welfare
[Specialized Research Management Institution] Korea Health Industry Development Institution
[Research Business Title] Medical device technology development (R&D)
[Research Project Title] Development of efficacy and safety evaluation system for implantable silicone implants with anti-fibrosis formation functionality
[Contribution Rate]1/1
[Main Research Institution] Seoul National University Bundang Hospital
[Research Period] Nov. 1, 2015-Oct. 31, 2020

BACKGROUND ART

Recently, as life expectancy after treatment due to breast-related diseases such as breast cancer is increased and the cosmetic aspect is emphasized, various methods of reconstructing a breast after mastectomy are in common use.

As an example of the method of reconstructing the breast described above, a breast reconstruction surgery in which a tissue expander is primarily inserted to stretch a soft tissue to a degree at which an implant may be inserted, and then secondarily, the tissue expander is replaced with a permanent implant is used.

In case that the breast reconstruction surgery is performed, the tissue expanders or the implants are foreign substances and thus may cause capsular contracture after entering the breast area. For reference, the capsular contracture is a symptom in which a thick film is formed around the inserted tissue expander or implant and tactile feel thereof is gradually hardened, accompanied by inflammation etc. therefrom. When a side effect such as inflammation etc. occurs, it is usual that the tissue expander or the implant is merely removed and treated through a subsequent surgery.

Therefore, the present inventors have intensively studied a method of monitoring and treating the capsular contracture when the breast reconstruction surgery is performed and the inflammation etc. therefrom in real time as much as possible, and to this end reached the present invention.

DISCLOSURE

Technical Problem

In an aspect, an object of the present disclosure is to provide a device in which a patient or a medical staff may easily check or evaluate capsular contracture that may occur when wearing a tissue expander for breast reconstruction and a side effect such as inflammation etc. therefrom in real time even from outside the human body.

In another aspect, an object of the present disclosure is to provide a system which may store information transmitted from the tissue expander in real time and cumulatively and in which a medical staff and a patient may share the information.

Solution to Problem

In an aspect, the present disclosure provides a tissue expander for breast reconstruction comprising: an MMP sensor unit attached to the tissue expander, in which the MMP sensor unit comprises a biosensor configured to detect matrix metalloproteinase (MMP), which is collagenase, of surrounding tissues adjacent to the tissue expander.

In an example, the MMP sensor may be a biosensor comprising an MMP-specific peptide in which a change in electrical current is induced when cleaved by the MMP. In addition, the MMP sensor may be an MMP-specific redox reporter-peptide biosensor which further includes redox reporter substance.

The tissue expander may detect capsular contracture depending on whether collagenase is detected.

In another aspect, the present disclosure provides a patient information system that performs a wireless communication with the above-described tissue expander, and that receives tunneling electrical current signal information due to the MMP from the tissue expander and provides information on whether the capsular contracture occurred.

In still another aspect, the present disclosure provides a user terminal that performs a wireless communication with the above-described tissue expander, and that receives tunneling electrical current signal information due to the MMP from the tissue expander and provides information on whether the capsular contracture occurred.

Advantageous Effects of the Invention

According to the present disclosure, a patient or a medical staff may easily check and evaluate capsular contracture that may occur when wearing a tissue expander for breast reconstruction and a side effect such as inflammation etc. therefrom in real time even from outside the human body, thereby enabling effective treatment and response before or when the capsular contracture occurs.

In addition, the information transmitted from the tissue expander may be stored in a hospital system and/or a user terminal of the medical staff or the patient in real-time and cumulatively and shared by the medical staff and the patient, thereby helping medical examination and treatment as well as helping to establish the treatment plan.

DESCRIPTION OF REFERENCE NUMBERS

Figure 1:
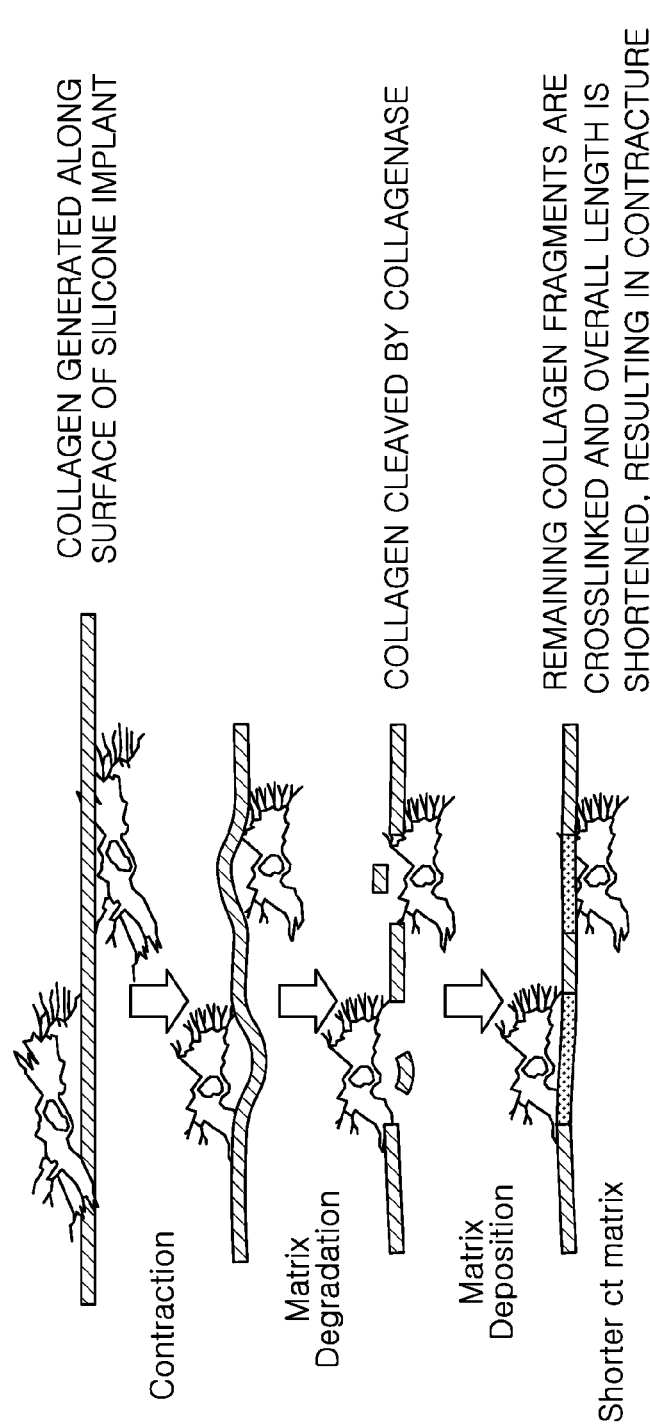
FIG. 1 is a schematic view showing a principle of capsular contracture.

10: Protrusion
20: Circumferential portion
30: Drug port
31: Drug release channel
32: Drug outlet
33: Drug movement channel
34: Drug port inlet
35: Drug port separation wall
36: Hole
40: Expansion port
41: Expansion port inlet
50: Protrusion type suture portion
100: Sensor unit
150: Sensor
E: Tissue expander
P: Port unit

MODE FOR INVENTION

In the present specification, terms such as "unit", "module", "device", "terminal", "sensor", and "system" etc. may refer to not only hardware but also a combination of software driven by the corresponding hardware. For example, the hardware may be a data processing device including a CPU or other processors. In addition, software driven by hardware may be a program such as an executing process, an object, an executable file, a thread of execution, or a computation program, etc.

In the present specification, an MMP sensor is not limited as long as it is a biosensor capable of detecting MMP and may include a known biosensor for detecting MMP. For example, as described later, the biosensor may be an electrical current change measurement biosensor including a peptide cleavable by MMP and a redox reporter that causes a change in electron movement (oxidation-reduction reaction) depending on a distance from an electrode (tunneling state), that is, an MMP-specific peptide biosensor.

Hereinafter, the present disclosure will be described in detail with reference to the accompanying drawings.

A tissue expander for breast reconstruction according to exemplary embodiments of the present disclosure includes an MMP sensor unit attached to a tissue expander. The MMP sensor unit includes a biosensor configured to detect matrix metalloproteinase (MMP), which is collagenase, of the surrounding tissues adjacent to the tissue expander, and may detect capsular contracture depending on whether the collagenase is detected, so it is possible to monitor the capsular contracture in real time.

FIG. 1 is a schematic view showing a principle of capsular contracture.

As shown in FIG. 1, the actual reason for contracture is that collagen fiber generated along the surface of a silicone artificial breast implant or a tissue expander is cleaved by collagenase and the remaining fragments are cross-linked again, thereby eventually causing the contracture due to the shortening of the length of the collagen fiber surrounding the implant. That is, since collagenase plays the most decisive role in capsular contracture, it is possible to eventually detect the capsular contracture by detecting this collagenase.

Accordingly, in the exemplary embodiments of the present disclosure, a sensor configured to detect collagenase, that is, matrix metalloproteinase (MMP) is mounted on the tissue expander.

In an example, a known sensor may be used as for the biosensor which detects the MMP.

For example, the biosensor configured to detect the MMP is a biosensor including a redox reporter substance such as methylene blue, for example, in which the movement of electrons changes when the peptide is cleaved by MMP, and an MMP-specific peptide (i.e., MMP-specific redox reporter-peptide).

In other words, by detecting electron movement between the electrode and the methylene blue which is generated as methylene blue (MB) connected to a terminal of the peptide moves away from the electrode when the peptide is cleaved by MMP, that is, a tunneling electrical current (hereinafter, referred to as tunneling electrical current according to MMP), it is possible to detect the MMP and eventually detect the contracture. The MMP-specific redox reporter-peptide biosensor is advantageously applied to the tissue expander for breast reconstruction according to the embodiments of the present disclosure in that it is possible to relatively easily detect the capsular contracture according to a change in electrical current.

In an example, a concentric electrode may be used to integrate such a biosensor with a COMS circuit, and thus, the MMP may be quantitatively detected through a difference in electrical current by each concentration of the MMP and/or time.

In an example, the MMP sensor is preferably a sensor configured to detect MMP2 or MMP9.

Specifically, in the embodiments of the present disclosure, by mounting a biosensor including a methylene blue (MB)-peptide, which is a peptide specifically cleaved by MMP2 or MMP9, on the tissue expander, it is possible to quantitatively detect MMP2 or MMP9 expressed upon capsular contracture to quantitatively detect the degree of the capsular contracture in real time.

Figure 2:
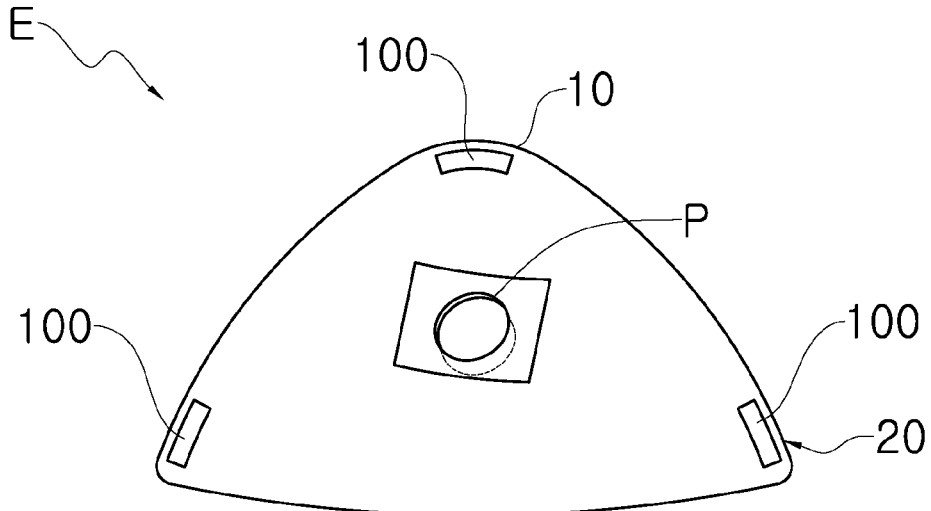
FIG. 2 is a schematic view showing a tissue expander for breast reconstruction according to an example of the present disclosure.

FIG. 2 is a schematic view showing a tissue expander for breast reconstruction according to an example of the present disclosure.

As shown in FIG. 2, in an example, the tissue expander includes a body having a protrusion 10 formed on a part thereof and a circumferential portion 20 integrally formed to be inclined or curved in an outward direction with respect to the protrusion 10. In addition, the body may include one or more port units 30 allowing for injection of an expansion solution into the tissue expander and/or a therapeutic drug.

In addition, one or a plurality of MMP sensor units 100 may be formed in the tissue expander.

In an example, the MMP sensor units 100 may be located to be spaced apart from each other on a surface of the tissue expander.

In this regard, the biosensor detects a signal generated by a substance (target) to be detected and a bioreceptor that may selectively react thereto, and it is necessary to increase selectivity to react specifically with a desired target among countless chemical and biological substances. Therefore, the MMP sensor units 100 may be preferably formed at a portion of the tissue expander that is most likely to come into contact with the human tissue in terms of increasing the sensing efficiency.

Accordingly, the MMP sensor units 100 may be located on the surface of the tissue expander.

Herein, each MMP sensor units 100 may be preferably formed on at least the protrusion 10 and the circumferential portion 20. As an example, one MMP sensor unit 100 may be formed on the protrusion 10, and one MMP sensor unit 100 may be respectively formed at both sides of the circumferential portion 20, but the present disclosure is not limited thereto.

Figure 3A:
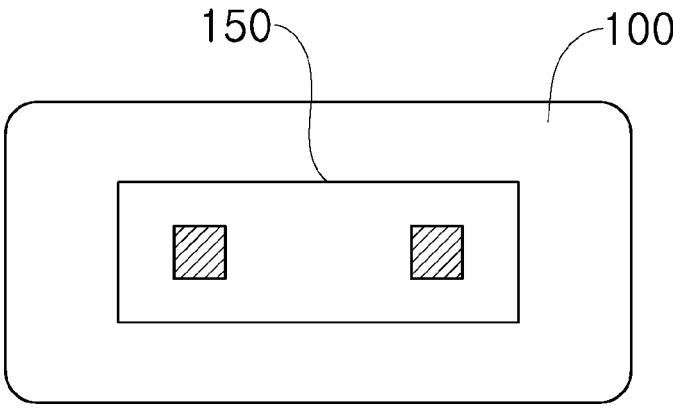
FIG. 3A is an enlarged view of an MMP sensor in FIG. 2.

FIG. 3A is an enlarged view of an MMP sensor in FIG. 2.

As shown in FIG. 3A, the MMP sensor unit 100 of the tissue expander may include a biocompatible silicon substrate formed on at least a part of the surface of the tissue expander; one or more MMP sensor 150 attached to the silicon substrate and including redox reporter [e.g., methylene blue (Mb)]-peptide specifically cleaved by MMP such as MMP2 or MMP9 to change the movement of electrons; a current detection module configured to detect a change in electrical current from the MMP sensors; and a transmission module configured to transmit the detected current signal to an external device.

Figure 3B:
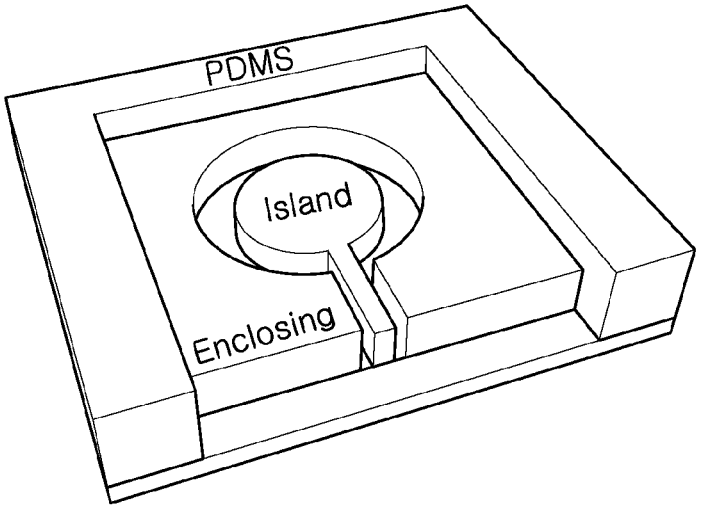
FIGS. 3B and 3C are schematic enlarged views of a structure of an MMP sensor.
Figure 3C:
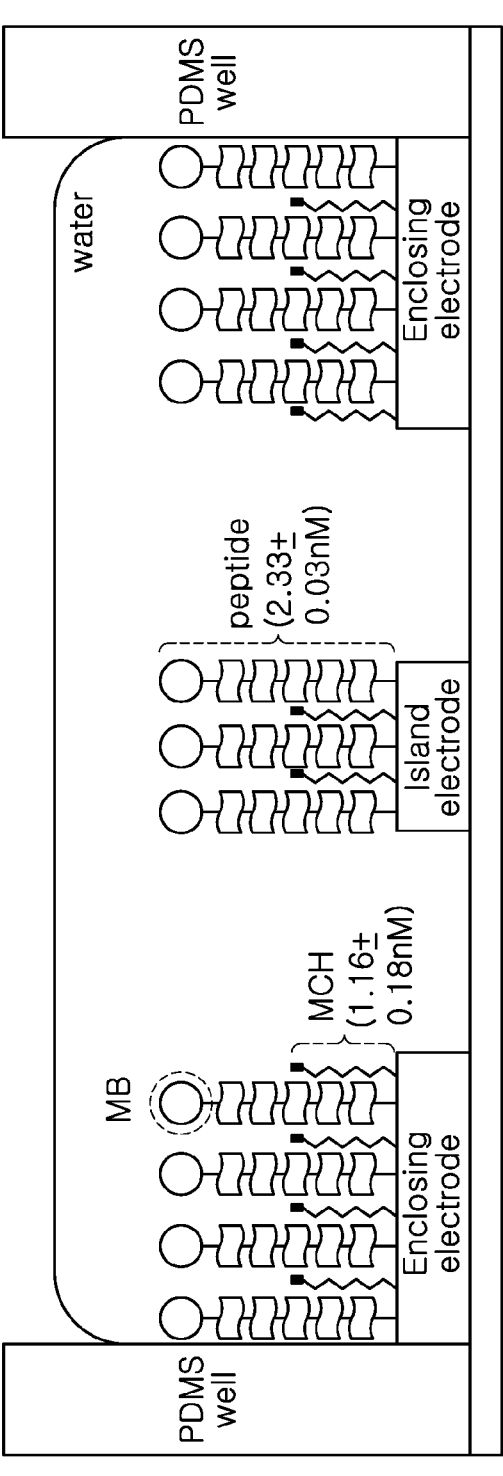

FIGS. 3B and 3C are a schematic enlarged view of a structure of the MMP sensor used in an example of the present disclosure.

In order to attach a peptide synthesized with methylene blue, which is a redox reporter, to a plurality of electrodes (e.g., Au electrode) deposited on a silicon oxide film formed on a solid substrate such as a silicon chip, first, the electrode and the peptide may be connected through a thiolate bond between Cys at the terminal of the peptide and the gold electrode using a well-shaped PDMS.

In an example, the peptide cleavable by MMP2 or MMP9 may be designed to contain methylene blue (MB) serving as a redox reporter, that is, a tunneling state.

Specifically, when MB-Gly-Pro-Leu-Gly-Met-Trp-Ser-Arg-Lys-Cys (MB-GPLGMWSRKC), which is an MMP2 or MMP9-specific MB-peptide, is used, Gly and Met may be cleaved by MMP2 or MMP9, thereby the movement of electrons is changed and MMP2 or MMP9 is sensed. In addition, at this time, the degree of the movement of electrons may correspond to the concentration of MMP2 or MMP9.

Meanwhile, the MMP sensor unit 100 may include a current measurement module configured to measure a tunneling electrical current of electrons from the MMP sensor.

The corresponding electrical current measurement module may use a concentric structured electrode as shown in FIG. 3A in order to integrate the biosensor with a CMOS circuit for signal processing.

The concentric electrode structure is a two-electrode structure of an island electrode detecting a tunneling electrical current signal that holds a potential and an enclosing electrode surrounding the island electrode. Since areas of the island electrode and the enclosing electrode differs by 1000 times or more, a self-gating effect in which a potential of the aqueous solution is fixed to a voltage of the enclosing electrode due to the difference in capacitance of the electrical double layer to the aqueous solution occurs, so it is possible to detect the change in electrical current by MMP even without a reference electrode.

Meanwhile, in an example, the detected tunneling electrical current signal that changes depending on the number of methylene blues fixed to the gold electrode may be transmitted wirelessly to a user terminal and/or a patient information system outside the human body as described later through a medical device radio communication service (MedRadio) frequency band.

For reference, the MB-peptide is fixed to the gold electrode and then the electrical current may be measured by using cyclic voltammetry at a voltage of initially applied −0.4 V and then double-swept up to 0.2 V and a scan rate of 10 V/sec. In an equilibrium state in which a voltage is not applied, two states of MB+ and leucomethylene blue (LMB), which is a reduction substance of methylene blue, coexist. When a voltage of −0.4 V is continuously applied, a tunneling of electrons occurs from the gold electrode to MB+, and as a result, all of interfaces of the biosensor are changed to LMB so that an electrical current may be measured.

Thereafter, when the electrical current is measured while the voltage is swept to 0.2 V, the tunneling of electrons occurs from LMB to the electrode. When the voltage is swept to 0.2 V and then swept back to −0.4 V, at this time, the tunneling of electrons occurs from the electrode to MB+, contrary to the positive voltage sweep. Accordingly, as the MB-peptide is cleaved by MMP, the MB serving as a site for tunneling of electrons is separated along with the peptide, so it is possible to observe that the electrical current gradually decreases over time.

Meanwhile, in an example, the MMP sensor unit 100 may be charged by using a known wireless power transfer (WPT) technology.

In addition, in an example, the sensor may be manufactured for a single chip by embedding an ultra-small MMP sensor unit 100 of, for example, 0.4×1.0 mm. For example, the corresponding MMP sensor unit may be manufactured as a chip-type structure in which an antenna for wireless communication, a coil for wireless charging, and a secondary battery are integrated with the sensor. The coil for wireless charging of the corresponding structure receives power from an external device to transmit power to the secondary battery. In addition, an external base station for wireless power supply may be additionally provided.

Such an MMP sensor unit may not only sense the capsular contracture, but also prevent or treat the capsular contracture.

That is, in an example, the MMP sensor may include an MMP-specific peptide, and an MMP inhibitor or an inhibitory drug may be bonded to the terminal of the peptide. For example, corticosteroid and doxycycline, which are drugs that inhibit MMP2 or MMP9, are bonded with glycine, which is the terminal of the peptide, so that the drug can be released when the peptide is cleaved by MMP2 or MMP9. Accordingly, the inhibition of MMP2 or MMP9 may consequently prevent the capsular contracture.

Meanwhile, in another example, when contracture is detected through the sensor, a medical staff may inject a drug through a separate drug port so that the tissue expander may release the drug to the surrounding tissues.

Figure 4A:
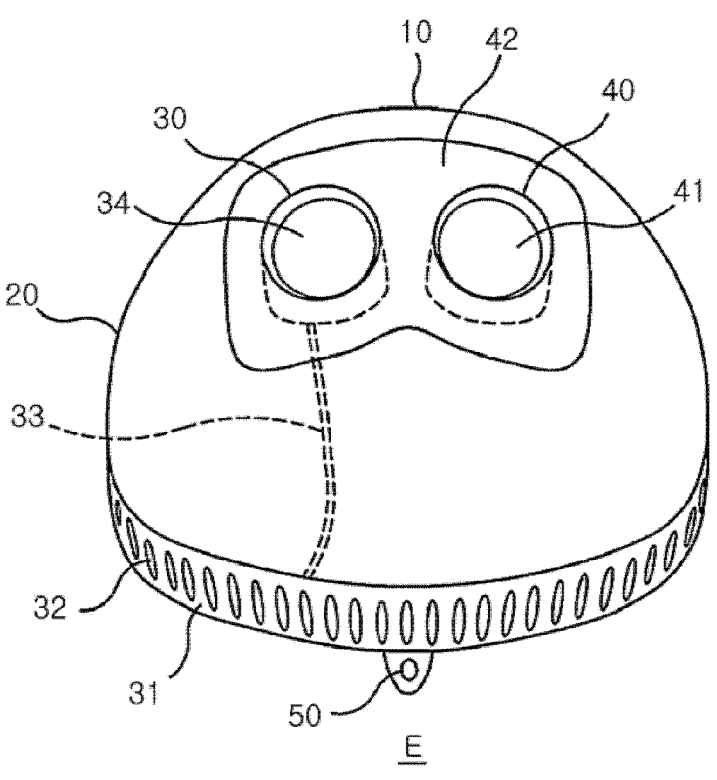
FIGS. 4A and 4B are schematic views showing a tissue expander additionally provided with a drug port according to another example of the present disclosure.
Figure 4B:
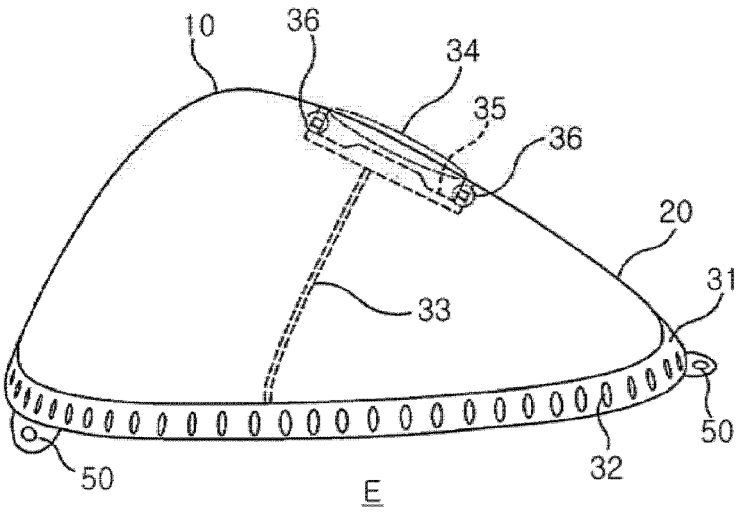

FIGS. 4A and 4B are schematic views showing a tissue expander additionally provided with a drug port according to another example of the present disclosure.

As shown in FIGS. 4A and 4B, for drug injection/release, the body of the tissue expander may be additionally provided with a drug port 30 along with an expansion port 40.

The expansion port 40 includes an inlet 41 through which the expansion solution is injected and a storage unit 42 capable of storing the injected expansion solution.

The drug port 30 for drug injection/release is a port formed separately from the expansion port 40 and may include a soft inlet 34 and a rigid separation wall 35. The drug injected through the inlet 34 moves through a hole 36 that exists on at least one surface of the separation wall 35 to move to a drug release channel 31 at the terminal of the body through a drug movement channel 33 and may be transmitted into the body through multiple drug outlets 32. The drug release channel 31 may be provided with at least two or more protrusion type suture portions 50 for fixing and supporting.

As described above, the above-described MMP electrical current change signal collected from the sensor may be transmitted to a patient information management system or a user terminal to be described later, and when it is determined that the capsular contracture is detected based on the signal, after the medical doctor's treatment, the drug may be injected through the drug port 30, thereby allowing the drug to be released into human tissues.

The drug injected into the drug port 30 may be a drug injected for treating the capsular contracture that may occur due to the tissue expander implanted in the body, and as an example, may include a fibrosis inhibitor, an anti-prolifera-tive agent, an anti-ischemia complexes, anticoagulants, etc.

The fibrosis inhibitor may specifically include pirfeni-done, mitomycin, acetylsalicylic acid, genistein, selenocys-tine, or tranilast, etc., but is not limited thereto.

The proliferation inhibitor may specifically include tamoxifen, halofuginone, vitamin C, asiaticoside, cyclosporine A, homoharringtonine, vitamin A, D-penicil-lamine, or liposomes, etc., but is not limited thereto.

The anti-ischemic complex may specifically include Necrox-5 or Necrox-7, and the anticoagulant may specifi-cally include a tissue type plasminogen activator, urokinase (thrombolytic agent), heparin, or suramin, etc., but is not limited thereto.

Meanwhile, in other exemplary embodiments of the pres-ent disclosure, there is provided a patient information sys-tem configured to perform a wireless communication with the above-described tissue expander, and the system receives the MMP electrical current change signal informa-tion from the tissue expander and provides information on whether the capsular contracture occurred.

In addition, in still another exemplary embodiment of the present disclosure, there is provided a user terminal config-ured to perform a wireless communication with the above-described tissue expander, and the user terminal receives the MMP electrical current change signal information from the tissue expander and provides information on whether the capsular contracture occurred.

Figure 5:
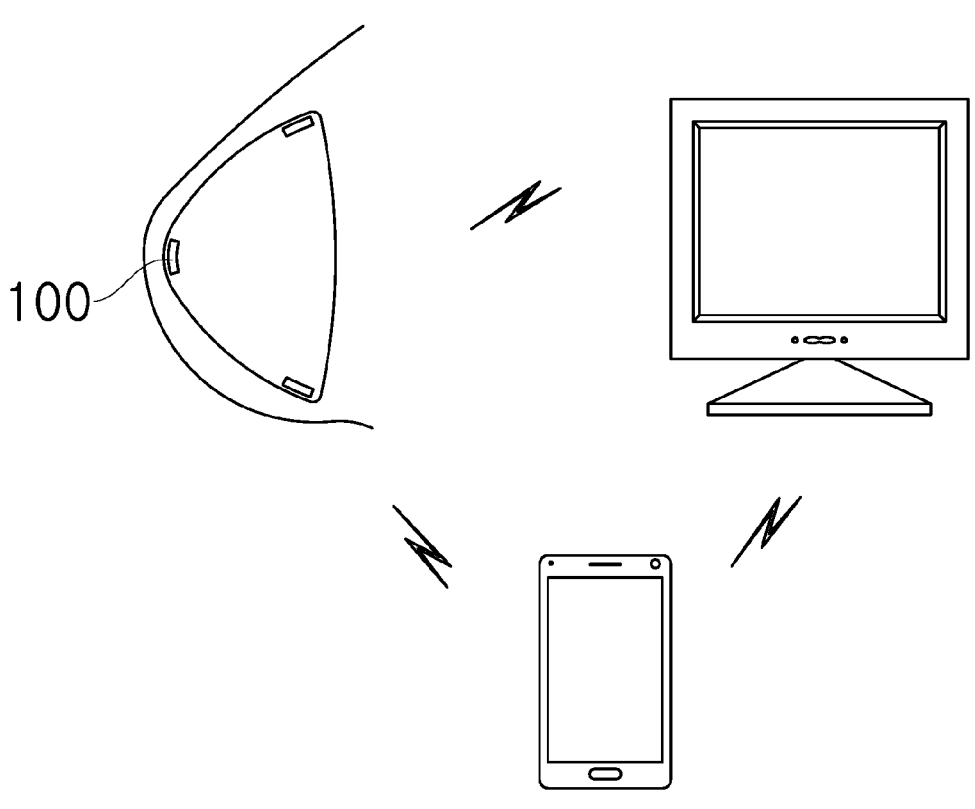
FIG. 5 schematically shows a user terminal and a patient information management system linked to a tissue expander according to an example of the present disclosure.

FIG. 5 schematically shows a user terminal and patient information management system linked to the tissue expander according to an example of the present disclosure.

In an example, when receiving an MMP electrical current change signal of a certain level or more from the sensor, the patient information system and/or the user terminal may provide an alarm signal related to the capsular contracture. Herein, for an amount of MMP that may be suspected as the capsular contracture, its appropriate concentration may be predicted through an in vitro/in vivo experiment.

As described above, the real-time capsular contracture monitoring is possible by the tissue expander equipped with the MMP sensor unit, and its result may be provided to a patient information management system of a hospital or a user terminal of a medical staff and/or a patient in real time and cumulatively. As a result, a patient or a medical staff may easily check and evaluate the capsular contracture and a side effect such as inflammation etc. therefrom in real time even from outside the human body, thereby enabling the preemptive treatment and response before the capsular con-tracture occurs and also helping medical examination and treatment as well as helping to establish the treatment plan.

INDUSTRIAL APPLICABILITY

According to the present disclosure, a patient or a medical staff may easily check and evaluate capsular contracture that may occur when wearing the tissue expander for breast reconstruction and a side effect such as inflammation there-from in real time even from outside the human body, thereby enabling effective treatment and response before or when the capsular contracture occurs. In addition, the information transmitted from the tissue expander may be stored in a hospital system and/or a user terminal of the medical staff or the patient in real-time and cumulatively and shared by the medical staff and the patient, thereby helping medical examination and treatment as well as helping to establish the treatment plan.

The invention claimed is:

1. A tissue expander for breast reconstruction comprising:
an MMP sensor unit attached to the tissue expander,
wherein the MMP sensor unit comprises a biosensor configured to detect matrix metalloproteinase (MMP), which is collagenase, of surrounding tissues adjacent to the tissue expander, wherein the biosensor comprises an MMP-specific peptide in which a change in electri-cal current is induced when the peptide is cleaved by the MMP.

2. The tissue expander for breast reconstruction according to claim 1,
wherein the biosensor is an MMP-specific redox reporter-peptide biosensor which comprises a peptide in which the change in electrical current is induced when the peptide is cleaved by the MMP and further comprises a redox reporter substance.

3. The tissue expander for breast reconstruction according to claim 1,
wherein the MMP sensor unit comprises: one or more MMP sensors; a current detection module configured to detect a change in electrical current from the MMP sensor; and a transmission module configured to trans-mit a detected current signal to outside.

4. The tissue expander for breast reconstruction according to claim 1,
wherein the MMP sensor comprises an MMP2- or MMP9-specific peptide.

5. The tissue expander for breast reconstruction according to claim 1,
wherein the tissue expander comprises a body having a protrusion formed on a part thereof and a circumfer-ential portion integrally formed to be inclined or curved in an outward direction with respect to the protrusion, and
the body further comprises a port unit allowing for injection of an expansion solution to be injected into the tissue expander, and
one or a plurality of MMP sensor units located on at least one side of a surface of the body.

6. The tissue expander for breast reconstruction according to claim 1,
wherein the tissue expander comprises a chip type struc-ture in which an antenna for wireless communication, a coil for wireless charging, and a secondary battery are integrated with the MMP sensor unit.

7. The tissue expander for breast reconstruction according to claim 1,
wherein the MMP sensor includes an MMP-specific pep-tide, and an MMP inhibitor or inhibitory drug is further bonded to a terminal of the peptide.

8. The tissue expander for breast reconstruction according to claim 1,
wherein the tissue expander further comprises a drug port at the body.

9. The tissue expander for breast reconstruction according to claim 8,
wherein a drug release channel comprising a plurality of drug outlets is provided at an end of a circumferential portion of the tissue expander, and

the drug port and the drug release channel are connected to a drug movement channel.

10. A patient information system, wherein the system performs a wireless communication with the tissue expander of claim 1, and wherein the system receives MMP current change signal information from the tissue expander and provides information on whether capsular contracture occurred.

11. A user terminal, wherein the user terminal performs a wireless communication with the tissue expander of claim 1, and wherein the user terminal receives MMP current change signal information from the tissue expander and provides information on whether capsular contracture occurred.

12. The user terminal according to claim 11, wherein the user terminal provides an alarm signal related to the capsular contracture when receiving the MMP current change signal information.

13. The patient information system according to claim 10, wherein the patient information system provides an alarm signal related to the capsular contracture when receiving the MMP current change signal information.

\* \* \* \* \*

10